United States Patent [19]
> Hoffmann

[11] 4,356,127
[45] Oct. 26, 1982

[54] PREPARATION OF 3-(2,2-DICHLORO-VINYL)-2,2-DIMETHYL-CYCLOPROPANE-1-CARBOXYLIC ACID DERIVATIVES

[75] Inventor: Hellmut Hoffmann, Wuppertal, Fed. Rep. of Germany

[73] Assignee: Bayer Aktiengesellschaft, Leverkusen, Fed. Rep. of Germany

[21] Appl. No.: 165,928

[22] Filed: Jul. 2, 1980

[30] Foreign Application Priority Data

Jul. 21, 1979 [DE] Fed. Rep. of Germany ....... 2929670

[51] Int. Cl.$^3$ ................. C07C 120/00; C07C 121/48; C07C 69/743; C07C 69/747
[52] U.S. Cl. ..................... 260/464; 260/940; 260/941; 260/946; 260/953; 260/544 L; 560/124; 564/190; 568/361
[58] Field of Search .................. 560/124; 568/361; 260/464; 564/190

[56] References Cited

U.S. PATENT DOCUMENTS

| | | | |
|---|---|---|---|
| 3,139,377 | 6/1964 | Ratts | 570/193 X |
| 3,247,265 | 4/1966 | Speziale et al. | 570/217 X |
| 3,737,450 | 6/1973 | Henrick et al. | 560/124 |
| 3,793,375 | 2/1974 | Schwieter et al. | 568/361 X |

FOREIGN PATENT DOCUMENTS

2326077  1/1974  Fed. Rep. of Germany .

OTHER PUBLICATIONS

Fieser et al., Reagents for Organic Synthesis, vol. 1, (1967), pp. 223 and 250; vol. 2, (1969), pp. 131–132 and 155; vol. 3, (1972), p. 97; vol. 4, (1974), pp. 150–151; vol. 6, (1977), pp. 188, 189, 191, 193; vol. 7, (1979), pp. 104, 106–107, 125, 126, John Wiley & Sons, New York.
"The Merck Index," 8th Ed., (1968), pp. 1226–1227.
Horner, et al., Chem. Ber. 103, pp. 2984–2986, (1970).
Savignac, et al., Synthesis, 1975, pp. 535–536.
Berlin, et al., J.A.C.S., 86, (1964), pp. 3862–3866.
Houben–Weyl, Methodender Organischenchemie, 4th Ed, vol. 12/1, p. 453, (1963).
Furukawa, et al., J.A.C.S., 89, (1967), pp. 3912–3914.
Payne, J. Org. Chem., 32, (1967), pp. 3351–3355.
Devos, et al., Tetrahedron Letters, (1978), pp. 1847–1850.
Kristensen, et al., Bull. Soc. Chim. Belg., 87, (1978), pp. 721–732.
Savignac, et al., Tetrahedron Letters, (1975), pp. 609–610.
Elkaim, et al., Tetrahedron Letters, (1975), pp. 4409–4410.

*Primary Examiner*—Joseph Paul Brust
*Attorney, Agent, or Firm*—Sprung, Horn, Kramer & Woods

[57] ABSTRACT

A process for the preparation of a 3-(2,2-dichlorovinyl)-2,2-dimethyl-cyclopropane-1-carboxylic acid derivative of the formula

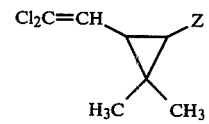

in which
Z is acetyl, cyano, carbamoyl, alkoxycarbonyl or —COOZ$^1$, and
Z$^1$ is a radical customary in the alcohol part of pyrethroids, comprising reacting an α-hydroxy-phosphonic acid ester of the formula

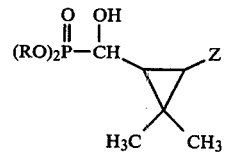

in which
R each independently is alkyl or phenyl, or the two radicals R togehter are alkanediyl,
with a dichloromethane derivative of the formula

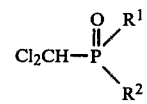

in which
R$^1$ and R$^2$ each independently is alkyl, phenyl, alkoxy or phenoxy, or together are alkanedioxy,
in the presence of a base and at a temperature between about −100° and +100° C.

6 Claims, No Drawings

PREPARATION OF 3-(2,2-DICHLORO-VINYL)-2,2-DIMETHYL-CYCLOPROPANE-1-CARBOXYLIC ACID DERIVATIVES

The invention relates to an unobvious process for the preparation of certain 3-(2,2-dichloro-vinyl)-2,2-dimethyl-cyclopropane-1-carboxylic acid derivatives, some of which are known.

It is known that 3-(2,2-dichloro-vinyl)-2,2-dimethyl-cyclopropane-1-carboxylic acid esters are obtained when 3-formyl-2,2-dimethyl-cyclopropane-1-carboxylic acid esters are reacted with triphenylphosphine in carbon tetrachloride (see DE-OS (German Published Specification) No. 2,326,077). However, the desired products are obtained in only moderate yields by this synthesis method.

It is also known that 1,1-dichloro-alkenes are obtained when lithium salts of dichloromethane-phosphonic acid esters are reacted with aldehydes or ketones (compare Synthesis 1975, 535–536). However, the preparation of the lithium salts of dichloromethane-phosphonic acid esters is relatively troublesome: they are obtained from chloromethane-phosphonic acid esters by reaction with butyl-lithium and carbon tetrachloride at −75° C., it being necessary to use thoroughly dried solvents, and an inert gas atmosphere being required.

The present invention now provides a process for the preparation of a 3-(2,2-dichlorovinyl)-2,2-dimethyl-cyclopropane-1-carboxylic acid derivative of the general formula

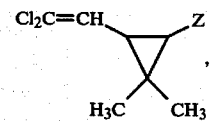
(I)

in which
Z represent acetyl, cyano, carbamoyl, alkoxycarbonyl or a radical —COOZ¹,
wherein
Z¹ represents a radical customary in the alcohol part of pyrethroids,
in which an α-hydroxy-phosphonic acid ester of the general formula

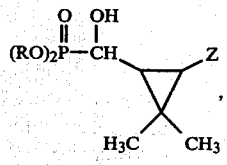
(II)

in which
Z has the meaning indicated above and
R represents alkyl or phenyl, or the two radicals R together represent straightchain or branched alkanediyl (alkylene),
is reacted with a dichloromethane derivative of the general formula

(III)

in which
R¹ and R² individually represent alkyl, phenyl, alkoxy or phenoxy or together represent alkanedioxy (alkylenedioxy),
in the presence of a base and if appropriate using a diluent, at a temperature between about −100° and +100° C.

It is surprising that 3-(2,2-dichloro-vinyl)-2,2-dimethyl-cyclopropane-1-carboxylic acid derivatives can be obtained in good yields in a considerably simpler and less expensive manner by the process according to the invention than could be expected in view of the state of the art.

If, for example, α-hydroxy-α-(3-methoxycarbonyl-2,2-dimethyl-cycloprop-1-yl)-methanephosphonic acid dimethyl ester and dichloromethane-phosphonic acid dimethyl ester are used as starting substances, the reaction of these compounds can be outlined by the following equation:

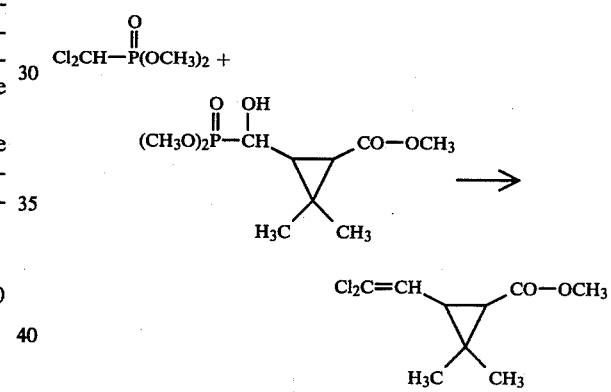

Formula (II) provides a definition of the α-hydroxy-phosphonic acid esters to be used as starting compounds. Preferably, in this formula.
Z represents acetyl, cyano, carbamoyl or ($C_1$-$C_4$-alkoxy)carbonyl and
R represents $C_1$-$C_4$-alkyl or phenyl, or the two radicals R together represent 2,2-dimethylpropane-1,3-diyl.

Examples of the compounds (II) which may be mentioned are: α-hydroxy-α-(3-methoxycarbonyl-2,2-dimethyl-cyclopropl-yl)-methanephosphonic acid dimethyl ester and diethyl ester, α-hydroxy-α-(3-ethoxycarbonyl-2,2-dimethyl-cycloprop-1-yl)-methane-phosphonic acid dimethyl ester and diethyl ester, α-hydroxy-α-(3-acetyl-2,2-dimethyl-cycloprop-1-yl)-methanephosphonic acid dimethyl ester and diethyl ester and α-hydroxy-α-(3-cyano-2,2-dimethyl-cycloprop-1-yl)-methanephosphonic acid dimethyl ester and diethyl ester.

The α-hydroxy-phosphonic acid esters of the formula (II) and their preparation are the subject of German patent application No. P 29 17 620.3.

The starting compounds of the formula (II) are obtained by reacting α-oxo-phosphonic acid esters of the general formula

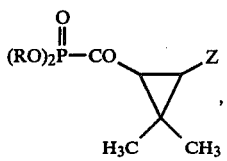

(IV)

in which Z and R have the meanings indicated above, with a reducing agent, for example sodium tetrahydridoborate (sodium boranate), if appropriate using a diluent, for example water and/or methanol and/or methylene chloride, at a temperature between −20° and +50° C., preferably between −10° and +30° C. (compare Chem. Ber. 103 (1970), 2984–2986). For working up and isolation of the products, the mixture is extracted with a water-immiscible solvent, for example methylene chloride, the non-aqueous phase is dried and filtered and the solvent is distilled off from the filtrate under reduced pressure.

The α-oxo-phosphonic acid esters of the formula (IV) have not hitherto been described in the literature. These compounds are obtained by reacting carboxylic acid chlorides of the general formula

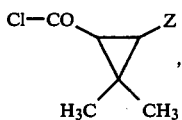

(V)

in which Z has the meaning indicated above, with phosphorous acid esters of the general formula $(RO)_2P-OR^3$ (VI), in which
R has the meaning indicated above and
$R^3$ represents alkyl, especially methyl or ethyl, at a temperature between −20° and +150° C. preferably between 0° and 120° C. (see J. Am. Chem. Soc. 86 (1964), 3862–3866 and Methoden der organischen Chemie (Methods of Organic Chemistry) (Houben-Weyl-Müller), 4th edition, Volume 12/1, page 453, Georg-Thieme-Verlag, Stuttgart (1963).

The products can be purified by vacuum distillation.

The hitherto unknown carboxylic acid chlorides of the formula (V) are obtained according to the equation below, from known cyclopropane-carboxylic acid esters (see J. Am. Chem. Soc. 89 (1967), 3912–3914; J. Org. Chem. 32 (1967), 3351–3355; Tetrahedon Lett. 1978, 1847–1850; and Bull Soc. Chim. Belg. 87 (1978), 721–732) by methods which are in themselves known, by first preparing the corresponding cyclopropanecarboxylic acids by hydrolysis, for example by reacting the esters with aqueous-alcoholic potassium hydroxide solution at a temperature between 20° and 100° C. and then acidifying the mixture, and reacting these acids with halogenating agents, for example thionyl chloride, at a temperature between 10° and 100° C.

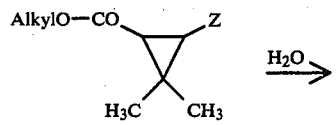

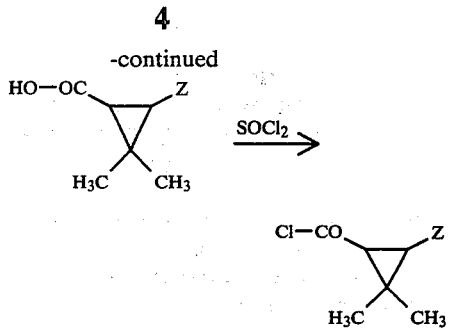

Formula (III) provides a definition of the dichloromethane derivatives also to be used as starting compounds. Preferably, in this formula, $R^1$ and $R^2$ individually represent alkoxy with 1 to 4 carbon atoms or phenoxy, or less preferably alkyl with 1 to 4 carbon atoms, or the two radicals $R^1$ and $R^2$ together represent straight-chain or branched alkanedioxy (alkylendioxy) with 2 to 5 carbon atoms.

Examples of the compounds (III) which may be mentioned ar dichloromethane-phosphonic acid dimethyl ester, diethyl ester and diphenyl ester.

Compounds of the formula (III) are known and can be prepared by processes which are known (see Synthesis 1975, 535–536; Tetrahedron Letters 1975, 609–610; and ibid., 1975, 4409–4410).

Dichloromethane-phosphonic acid esters of the formula (III) are obtained, for example, by reacting dichloromethane-phosphonic acid dichloride (see British patent specification No. 707,961) with sodium salts or potassium salts of hydroxy compounds, for example with sodium methylate, ethylate, n- or isopropylate or n-, iso-, sec.- or tert.-butylate or potassium methylate, ethylate, n- or iso-propylate or n-, iso-, sec.- or tert.-butylate, if appropriate in the presence of a diluent, for example toluene, at a temperature between 0° and 50° C. For purification, the products are distilled, if appropriate after filtration.

The process according to the invention is preferably carried out using a diluent. Possible diluents are virtually any of the inert organic solvents, especially aprotic polar solvents. These include ethers, for example glycol dimethyl ether, diglycol dimethyl ether, tetrahydrofuran and dioxane; carboxylic acid amides, for example dimethylformamide, dimethylacetamide and N-methylpyrrolidone; sulphoxides and sulphones, for example dimethylsulphoxide and tetramethylene sulphone; phosphoric acid amides, for example hexamethylphosphoric acid triamide, and nitriles, for example acetonitrile and propionitrile.

The bases customary in organochemical synthesis can be used in the process according to the invention. These bases include, as preferences, alkali metal hydroxides, for example sodium hydroxide and potassium hydroxide; alkali metal alcoholates, for example sodium methylate, potassium methylate, sodium ethylate, potassium ethylate, sodium isopropylate, potassium iso-propylate, sodium tert.-butylate and potassium tert.-butylate; alkali metal hydrides, for example sodium hydride and potassium hydride; alkali metal amides, for example, sodium amide and potassium amide; alkyl-lithium compounds, for example butyl-lithium; and amines, for example diazabicyclononane and diazabicycloundecene. Alcoholates are particularly preferred as the bases.

The reaction temperature is kept between −100° and +100° C., preferably from about −80° to +50° C. The process according to the invention is in general carried out under normal pressure.

1 to 3 mols, preferably 1 to 2 mols, of dichloromethane-phosphonic acid ester of the formula (III) are generally employed per mol of α-hydroxy-phosphonic acid ester of the formula (II).

In a preferred embodiment of the process according to the invention, the starting substances of the formulae(II) and (III) in one of the above-mentioned diluents are initially introduced into the reaction vessel at a temperature between −80° and 0° C. and a solution of a base in one of the above-mentioned diluents is added dropwise. The reaction mixture is then allowed to come to room temperature and is subsequently stirred for some hours. Working up is effected in the customary manner: the reaction mixture is diluted with water and extracted with a water-immiscible solvent, for example diethyl ether or methylene chloride. The extracts are washed with water, dried and filtered. The solvent is stripped off from the filtrate and the product remaining as the residue is purified by vacuum distillation. It is characterized by its boiling point.

Since the 3-formyl-2,2-dimethyl-cyclopropane-1-carboxylic acid esters of the formula (II) employed as starting compounds and also the 3-(2,2-dichloro-vinyl)-2,2-dimethyl-cyclopropane-1-carboxylic acid esters of the formula (I) to be prepared according to the invention each contain asymmetric carbon atoms, the compounds of the formulae (I) and (II) can occur in an appropriate number of stereoisomeric forms. The process according to the invention relates to the preparation of compounds of the formula (I) that are obtained either in the form of the individual stereoisomers or as mixtures of stereoisomers.

The 2,2-dimethyl-3-(2,2-dichloro-vinyl)-cyclopropane-1-carboxylic acid esters to be prepared by the process according to the invention can be used as intermediate products for the preparation of insecticidally and acaricidally active pyrethroids (see DE-OS (German Published Specification) No. 2,326,077).

PREPARATIVE EXAMPLE

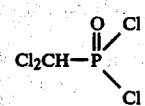 (a)

266 g (2 mols) of aluminum chloride were added in portions to a mixture of 720 g (6 mols) of chloroform and 274 g (2 mols) of phosphorus trichloride. The reaction mixture was then heated under reflux to the boiling point for 12 hours. The solvent was then stripped off in vacuo and the residue was taken up in 2 liters of methylene chloride. 440 ml of concentrated hydrochloric acid were added dropwise to this mixture at 0° C. and the mixture was subsequently stirred at this temperature for about two hours. The organic phase was separated off, dried over sodium sulphate and concentrated. The residue was subjected to fractional distillation. 258 g (64.5% of theory) of dichloromethane-phosphonic acid dichloride were obtained in the form of a colorless oil of boiling point 48°–50° C./1 mbar.

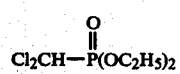 (b)

153.5 g (2.26 mols) of sodium methylate in 800 ml of ethanol were added dropwise to a solution of 227.5 g (1.13 mols) of dichloromethane-phosphonic acid dichloride in 800 ml of toluene at 5°–10° C. The reaction mixture was subsequently stirred at 20° C. for five hours. It was then filtered, the filtrate was concentrated and the residue was subjected to fractional distillation. 195 g (78% of theory) of dichloromethane-phosphonic acid diethyl ester were obtained in the form of a colorless oil of boiling point 84° C./1 mbar.

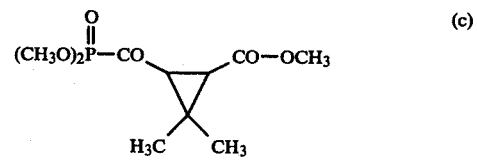 (c)

25 g (0.2 mol) of trimethyl phosphite were added dropwise to a solution, warmed to 30° to 35° C., of 39 g (0.2 mol) of 3-methoxycarbonyl-2,2-dimethyl-cyclopropane-1-carboxylic acid chloride in 200 ml of methylene chloride and the reaction mixture was stirred for 3 hours. After distilling off the solvent in vacuo, 48 g (91% of theory) of α-oxo-α-(3-methoxycarbonyl-2,2-dimethylcycloprop-1-yl)-methanephosphonic acid dimethyl ester were obtained.

Elementary analysis: calculated: C 45.5%; H 6.4%; O 36.4%; P 11.7%; found: C 44.9%; H 6.7%; O 36.6%; P 11.2%.

The following compound was obtained analogously:

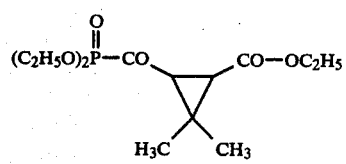

Elementary analysis: calculated: C 51.0%; H 7.5%; O 31.4%; P 10.1%; found: C 50.4%; H 7.4%; O 31.3%; P 9.7%.

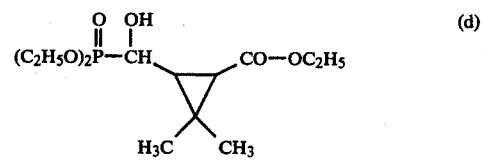 (d)

A solution of 31 g (0.1 mol) of α-oxo-α-(3-ethoxycarbonyl-2,2-dimethylcycloprop-1-yl)-methanephosphonic acid diethyl ester in 50 ml of methylene chloride was added dropwise to an intensively stirred solution of 1.2 g of sodium tetrahydridoborate in 75 ml of water at about 0° C. in the course of 30 minutes. The reaction mixture was stirred at 0° C. for 90 minutes. The organic phase was then separated off, the aqueous phase was extracted by shaking with 100 ml of methylene chloride, the methylene chloride solutions were combined, dried over sodium sulphate and filtered and the residue was concentrated. The residue was recrystallized from 30 ml of ligroin and the crystals were filtered off and dried on a clay plate. 19 g (62% of theory) of α-hydroxy-α-(3-ethoxycarbonyl-2,2-dimethyl-cycloprop- 1-yl)-methanephosphonic acid diethyl ester of melting point 58° C. were obtained.

Elementary analysis: calculated: C 50.6%; H 8.1%; O 31.2%; P 10.1%; found: C 50.7%; H 8.2%; O 30.5%; P 10.1%.

The following compound was obtained analogously:

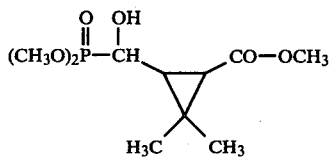

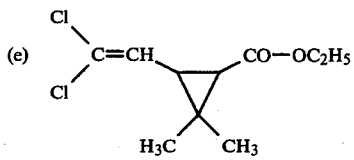   (1)

(e)

A solution of 22.5 g of potassium tert.-butylate in 150 ml of tetrahydrofuran was added dropwise to a solution of 31 g (0.1 mol) of α-hydroxy-α-(3-ethoxycarbonyl-2,2-dimethyl-cycloprop-1-yl)-methanephosphonic acid diethyl ester and 44 g (0.2 mol) of dichloromethane-phosphonic acid diethyl ester in 100 ml of tetrahydrofuran at −50° to −60° C. The temperature was allowed to rise slowly to about 20° C. and the mixture was stirred at this temperature for a further 35 hours. The reaction mixture was taken up in 500 ml of diethyl ether and the ether mixture was washed 4 times with 300 ml of water each time. The organic phase was dried over sodium sulphate and filtered and the filtrate was concentrated. The residue was distilled twice.

1st distillation: boiling point 100°–140° C./15 mbar;
2nd distillation: boiling point 114°–118° C./15 mbar.

21 g (89% of theory) of 2,2-dimethyl-3-(2,2-dichlorovinyl)-cyclopropane-1-carboxylic acid ethyl ester were thus obtained in the form of a colorless liquid which, according to analysis by gas chromatography, contained 76% of the trans-isomer.

The following compound was obtained analogously:

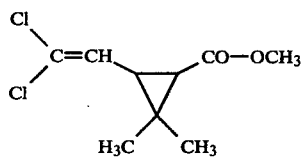   (2)

It will be appreciated that the instant specification and examples are set forth by way of illustration and not limitation, and that various modifications and changes may be made without departing from the spirit and scope of the present invention.

I claim:

1. A process for the preparation of a 3-(2,2-dichlorovinyl)-2,2-dimethyl-cyclopropane-1-carboxylic acid derivative of the formula

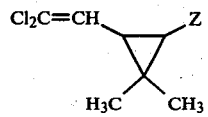

in which
Z is acetyl, cyano, carbamoyl or $C_{1-4}$-alkoxycarbonyl, comprising reacting an α-hydroxy-phosphonic acid ester of the formula

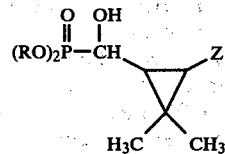

in which
R each independently is $C_{1-4}$-alkyl or phenyl, or the two radicals R together are 2,2-dimethyl-propane-1,3-diyl, with a dichloromethane derivative of the formula

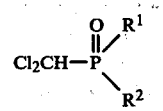

in which
$R^1$ and $R^2$ each independently is $C_{1-4}$-alkyl, phenyl, $C_{1-4}$-alkoxy or phenoxy, or together are $C_{2-5}$-alkane-dioxy, at a temperature between about −100° and +100° C. in a reaction phase consisting essentially of an inert aprotic organic liquid and in the presence of a base selected from the group consisting of an alkali metal hydroxide, an alkali metal alcoholate, an alkali metal hydride, an alkali metal amide, an alkyl-lithium compound or an amine.

2. A process according to claim 1, in which $R^1$ and $R^2$ each independently is alkoxy with 1 to 4 carbon atoms or phenoxy, or the two radicals $R^1$ and $R^2$ together are alkanedioxy with 2 to 5 carbon atoms.

3. A process according to claim 1, wherein the reaction is effected at about −80° to +50° C.

4. A process according to claim 1, wherein about 1 to 3 mols of the dichloromethane derivative are employed per mol of the α-hydroxy-phosphonic acid ester.

5. A process according to claim 1, wherein about 1 to 2 mols of the dichloromethane derivative are employed per mol of the α-hydroxy-phosphonic acid ester.

6. A process according to claim 2, in which the reaction is effected at about −80° to +50° C. and about 1 to 2 mols of the dichloromethane derivative are employed per mol of the α-hydroxy-phosphonic acid ester.

* * * * *